United States Patent [19]
Clark et al.

[11] Patent Number: 6,149,440
[45] Date of Patent: *Nov. 21, 2000

[54] METHODS AND APPARATUS FOR AUTHENTICATING INFORMED CONSENT

[75] Inventors: Robert L. Clark, Bellevue; Glen A. Morgan, Kent, both of Wash.

[73] Assignee: Wyngate, Inc., Bellevue, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 09/156,460

[22] Filed: Sep. 18, 1998

[51] Int. Cl.⁷ ..................................................... G09B 7/00

[52] U.S. Cl. ............................... 434/322; 434/350; 705/2

[58] Field of Search ..................................... 434/322, 362, 434/350, 323, 354, 321, 310, 315; 705/2, 3

[56] References Cited

U.S. PATENT DOCUMENTS

| | | |
|---|---|---|
| 3,273,260 | 9/1966 | Walker ........................................... 35/9 |
| 3,481,052 | 12/1969 | Dorsett .......................................... 35/8 |
| 3,504,445 | 4/1970 | Goldmark et al. ............................. 35/9 |
| 3,566,370 | 2/1971 | Worthington, Jr. et al. . |
| 3,794,982 | 2/1974 | McCormick et al. . |
| 3,839,708 | 10/1974 | Bredesen et al. . |
| 3,939,579 | 2/1976 | Andrews et al. ............................... 35/9 |
| 3,946,503 | 3/1976 | Buchan et al. ................................. 35/9 |
| 3,968,576 | 7/1976 | Taylor .......................................... 35/35 |
| 3,970,996 | 7/1976 | Yasaka et al. . |
| 4,053,951 | 10/1977 | Hudspeth et al. . |
| 4,085,446 | 4/1978 | Nagamura . |
| 4,130,881 | 12/1978 | Haessler et al. . |
| 4,205,387 | 5/1980 | Ovshinsky et al. . |
| 4,228,506 | 10/1980 | Ripley et al. . |
| 4,260,854 | 4/1981 | Kolodny et al. . |
| 4,346,449 | 8/1982 | Ovshinsky et al. . |
| 4,359,223 | 11/1982 | Baer et al. . |
| 4,360,345 | 11/1982 | Hon . |
| 4,395,236 | 7/1983 | Gotthold . |
| 4,459,114 | 7/1984 | Barwick . |
| 4,475,132 | 10/1984 | Rodesch . |
| 4,482,328 | 11/1984 | Ferguson et al. ........................ 434/310 |

(List continued on next page.)

FOREIGN PATENT DOCUMENTS

WO 93/23836  11/1993  WIPO .

OTHER PUBLICATIONS

Taylor, David A., "Object–Oriented Technology: A Managers Guide", Addison–Wesley Publishing Company, Inc. Jan. 1992.

Hume, Gregory D., "A Dynamic Student Model In a Cardiovascular Intelligent Tutoring System", Fifth Annual IEEE Symposium on Computer–Based Medical Systems, Jun. 14–17, 1992.

Barbour, G.L. et al., "Videotape Aids Informed Consent Decision", Journal of American Medical Association, Dec. 15, 1978; vol. 240, No. 25.

*Primary Examiner*—Jessica J. Harrison
*Assistant Examiner*—Chanda Harris
*Attorney, Agent, or Firm*—Wilson, Sonsini, Goodrich & Rosati

[57] ABSTRACT

The present invention relates generally to methods and apparatus for presenting selected information to one or more individuals, and authenticating both the individual's receipt and the individual's comprehension of the information presented. In a preferred embodiment of the present invention, the methods and apparatus relating to the authenticating operation include methods and apparatus for visually and, optionally, otherwise recording the individual's responses to the information presented simultaneously with the presentation thereof. Preferably the authenticating operation further includes methods and apparatus for archiving, retrieving and observing in a correlated fashion both the information presented and the recorded individual's responses thereto. The present invention is particularly well-suited to providing an individual with information apprising the individual of risks associated with a particular activity and authenticating the individual's receipt and comprehension of the information presented and informed consent to assume such risks when participating in such activity.

31 Claims, 6 Drawing Sheets

U.S. PATENT DOCUMENTS

| | | |
|---|---|---|
| 4,518,367 | 5/1985 | Hepp . |
| 4,552,535 | 11/1985 | Steffel ..................................... 434/315 |
| 4,569,421 | 2/1986 | Sandstedt . |
| 4,593,904 | 6/1986 | Graves . |
| 4,602,907 | 7/1986 | Foster . |
| 4,611,298 | 9/1986 | Schuldt . |
| 4,671,772 | 6/1987 | Slade et al. . |
| 4,685,122 | 8/1987 | Deveson et al. . |
| 4,771,344 | 9/1988 | Fallacaro et al. . |
| 4,812,125 | 3/1989 | Strashun . |
| 4,828,500 | 5/1989 | Seidel et al. . |
| 4,828,501 | 5/1989 | Ingenito et al. . |
| 4,839,743 | 6/1989 | Best et al. . |
| 4,846,693 | 7/1989 | Baer . |
| 4,863,384 | 9/1989 | Slade . |
| 4,893,270 | 1/1990 | Beck et al. . |
| 4,895,376 | 1/1990 | Chiang Shiung-Fei . |
| 4,907,146 | 3/1990 | Caporali . |
| 4,907,973 | 3/1990 | Hon . |
| 4,930,019 | 5/1990 | Chu . |
| 4,931,018 | 6/1990 | Herbst et al. . |
| 4,937,743 | 6/1990 | Rassman et al. . |
| 4,948,371 | 8/1990 | Hall . |
| 4,959,734 | 9/1990 | Foster . |
| 5,002,491 | 3/1991 | Abrahamson et al. . |
| 5,006,987 | 4/1991 | Harless . |
| 5,025,374 | 6/1991 | Roizen et al. . |
| 5,033,969 | 7/1991 | Kamimura . |
| 5,035,625 | 7/1991 | Munson et al. . |
| 5,059,127 | 10/1991 | Lewis et al. . |
| 5,065,315 | 11/1991 | Garcia . |
| 5,146,439 | 9/1992 | Jachmann et al. . |
| 5,167,506 | 12/1992 | Kilis et al. . |
| 5,276,775 | 1/1994 | Meng . |
| 5,289,531 | 2/1994 | Levine . |
| 5,303,042 | 4/1994 | Lewis et al. . |
| 5,321,605 | 6/1994 | Chapman et al. . |
| 5,395,336 | 3/1995 | Tantry et al. . |
| 5,553,609 | 9/1996 | Chen et al. . |
| 5,654,750 | 8/1997 | Weil et al. . |
| 5,799,282 | 8/1998 | Rakshit et al. . |
| 5,802,494 | 9/1998 | Kuno ....................... 702/2 X |
| 5,823,948 | 10/1998 | Ross, Jr. et al. . |
| 5,842,173 | 11/1998 | Strum et al. . |
| 5,848,901 | 12/1998 | Kim et al. ........................... 434/362 X |
| 5,999,909 | 12/1999 | Rakshit et al. ......................... 705/2 X |
| 6,014,630 | 1/2000 | Jeacock .................................. 702/3 X |
| 6,064,968 | 5/2000 | Schanz .................................. 705/1 X |

METHODS AND APPARATUS FOR AUTHENTICATING INFORMED CONSENT

BACKGROUND OF THE INVENTION

1. Field of the Invention

The present invention relates generally to methods and apparatus for presenting selected information to one or more individuals, and authenticating both the individual's receipt and the individual's comprehension of the information presented. In a preferred embodiment of the present invention, the methods and apparatus relating to the authenticating operation include methods and apparatus for visually and, optionally, otherwise recording the individual's response(s) to the information presented simultaneously with the presentation thereof. Preferably the authenticating operation further includes methods and apparatus for archiving, retrieving and observing in a correlated fashion both the information presented and the recorded individual's responses thereto. The present invention is particularly well-suited to providing an individual with information apprising the individual of risks associated with a particular activity and authenticating the individual's receipt and comprehension of the information presented and informed consent to assume such risks when participating in such activity.

2. Description of the Prior Art

Daily human interaction requires the exchange of ideas, language, symbols, data, messages, or other communications. In some situations, legal ramifications can arise if information is not communicated effectively.

Examples of information which, if miscommunicated or not fully appreciated by the recipient can give rise to legal ramifications are numerous. Such examples include, but are not limited to, information given to a patient regarding the risks associated with medical procedures or the use of medicinal drugs, information conveyed to person relating to the risks associated with certain leisure or sporting activities (e.g., but not limited to horse back riding, hang gliding, bungy jumping, parachuting, etc) and information conveyed which by nature of the information itself affects a persons legal rights, (e.g., legal effects of taking breathalyzer tests, legal effects associated with acknowledging receipt and understanding of Miranda warnings, legal effects of accepting a plea bargain in the context of criminal litigation or a settlement offer in the context of civil litigation).

Often, written consent forms are used by those conveying information to a recipient in an attempt to insulate the information provider from claims that the information was not provided or was not provided effectively. Such written consent forms either contain the information itself or are executed by the recipient after oral communication of the information to the recipient by the information provider. Such written consent forms typically state that the recipient's execution of the consent form evidences that the recipient has received and understood the information conveyed, and has consented to such risks as were described in the information conveyed to the recipient.

However, consent forms, standing alone, are not perfect instruments. A signed consent form does not necessarily provide insight into the recipient's state of mind, comprehension, or capacity. For example, there may be no indication of fraud, fatigue, misunderstanding, lapse of attention, coercion or other relevant factors which may have prevented the recipient from fully understanding the nature of the information conveyed, arguably rendering any such consent ineffective. If the consent is ineffective, the recipient could suffer physical, legal, pecuniary or other injury which was not necessarily contemplated by the recipient. The recipient might attempt to hold the information provider liable for such injury, for, among other grounds, failure to effectively communicate the information to the recipient. Therefore, uncertainty over whether the information was effectively communicated to and understood by the recipient could expose the information provider to liability despite the existence of a signed consent form.

Attempts have been made in the art to provide information to a recipient and to test the recipient's understanding of the information conveyed using audio-visual equipment as opposed to, or in addition to, the written consent form.

For example, U.S. Pat. No. 3,946,503 to Buchan et al. discloses a device that presents a pre-formatted audio-visual presentation to educate medical patients or other individuals about a subject. The visual portion of the presentation comprises a filmstrip and is displayed on an illuminated screen. The audio portion includes a synchronized audio tape. The Buchan device also discloses obtaining a patient's or individual's responses or answers to test questions in a condensed electrically coded form on a simple tape cassette. More particularly, by recording a series of tones on a cassette tape, the Buchan apparatus is able to link questions with the answers. To retrieve the user's responses, the audiotape is replayed whereupon the participant's responses are displayed as a plurality of illuminated lights. The Buchan apparatus also provides for bypassing a series of subordinate or branching sequences of questions in response to the selection of a predetermined answer to a primary question. The Buchan apparatus is adapted to record its data in condensed form and transmit that data by a data phone set to a remotely located computer which is programmed to process the data.

There are several limitations of the Buchan device. The Buchan device provides no visual or other authentication (e.g., electronic signature, retinal scan etc.,) conclusively establishing that a particular individual actually engaged in the learning session. Nor does the Buchan device provide an indication of the questioning environment, such as the degree of privacy, opportunities for fraud, coercion, etc. Nor does the Buchan device simultaneously record the recipient's visual and/or other response/reaction to the information presented simultaneously with the presentation thereof.

Additional audio-visual instruction devices are disclosed in U.S. Pat. Nos. 3,273,260; 3,939,579; 3,504,445; 4,482,328; 4,552,535; 3,481,052; and 3,968,576.

While generally adequate for displaying information to a person, these devices may not provide sufficient evidence of the recipient's receipt of the information and/or the recipient's demeanor, comprehension, or overall mental and physical state to adequately prove that a particular individual received certain information and was capable of understanding and fully appreciating the information conveyed.

A need exits in the art for a method and apparatus for presenting information to a recipient, which can conclusively establish that a particular individual received such information and fully comprehended such information, which method and apparatus is also capable of providing a correlated record of the information presented and the recipient's simultaneous responses to such information during its presentation, which correlated record can be archived, retrieved and observed for subsequent use at a later date. It would be particularly advantageous if such correlated record could be permanently, confidentially, and compactly stored.

SUMMARY OF THE INVENTION

The present invention is directed to methods and apparatus for presenting selected information to one or more individuals, and authenticating both the individual's receipt and the individual's comprehension of the information presented. In a preferred embodiment of the present invention, the methods and apparatus relating to the authenticating operation include methods and apparatus for visually and, optionally, otherwise recording the individual's response(s) to the information presented simultaneously with the presentation thereof. Preferably the authenticating operation further includes methods and apparatus for archiving, retrieving and observing in a correlated fashion both the information presented and the recorded individual's responses thereto.

In one embodiment of the present invention, a method for authenticating a recipient's receipt and comprehension of information includes the steps of:

providing a device for conveying information to a recipient;

selecting information to be provided to the recipient by the information conveying means;

recording at least one uniquely personal marker of said recipient to establish recipient's exposure to said information;

conveying said information to said recipient;

providing said recipient with at least one inquiry selected to determine said recipient's comprehension of the information conveyed;

directing said recipient to provide an answer to said inquiry;

recording each of said information conveyed, said inquiry and said recipient's answer to said inquiry while simultaneously visually recording said recipient as said recipient reviews said conveyed information, said inquiry and provides said answer; and correlatedly archiving on a storage medium said conveyed information, said inquiry, said answer and said visual recording of said recipient such that said conveyed information, said inquiry, said answer and said visual recording of said recipient are retrievable to simultaneously observe at least one element selected from the group consisting of said conveyed information, said inquiry, said answer and the corresponding visual record of said recipient reviewing said conveyed information, said inquiry or providing said answer.

The present invention is also directed to an apparatus for authenticating a recipient's receipt and comprehension of information comprising:

a device for conveying information to a recipient;

a means for selecting information to be provided to the recipient by the information conveying means;

a means for recording at least one uniquely personal marker of said recipient to establish recipient's exposure to said information;

a means for conveying said information to said recipient;

a means for providing said recipient with at least one inquiry selected to determine said recipient's comprehension of the information conveyed;

a means for directing said recipient to provide an answer to said inquiry;

a means for recording each of said information conveyed, said inquiry and said recipient's answer to said inquiry;

a means for simultaneously visually recording said recipient as said recipient reviews said conveyed information, said inquiry and provides said answer; and a means for correlatedly archiving on a storage medium said conveyed information, said inquiry, said answer and said visual recording of said recipient such that said conveyed information, said inquiry, said answer and said visual recording of said recipient are retrievable to simultaneously observe at least one element selected from the group consisting of said conveyed information, said inquiry, said answer and the corresponding visual record of said recipient reviewing said conveyed information, said inquiry or providing said answer.

DESCRIPTION OF THE PREFERRED EMBODIMENT

The present invention relates generally to methods and apparatus for presenting selected information to one or more individuals, and authenticating both the individual's receipt and the individual's comprehension of the information presented. The present invention is particularly well-suited to providing an individual with information apprising the individual of risks associated with a particular activity and authenticating the individual's receipt and comprehension of the information presented and informed consent to assume such risks when participating in such activity.

Figure 1:
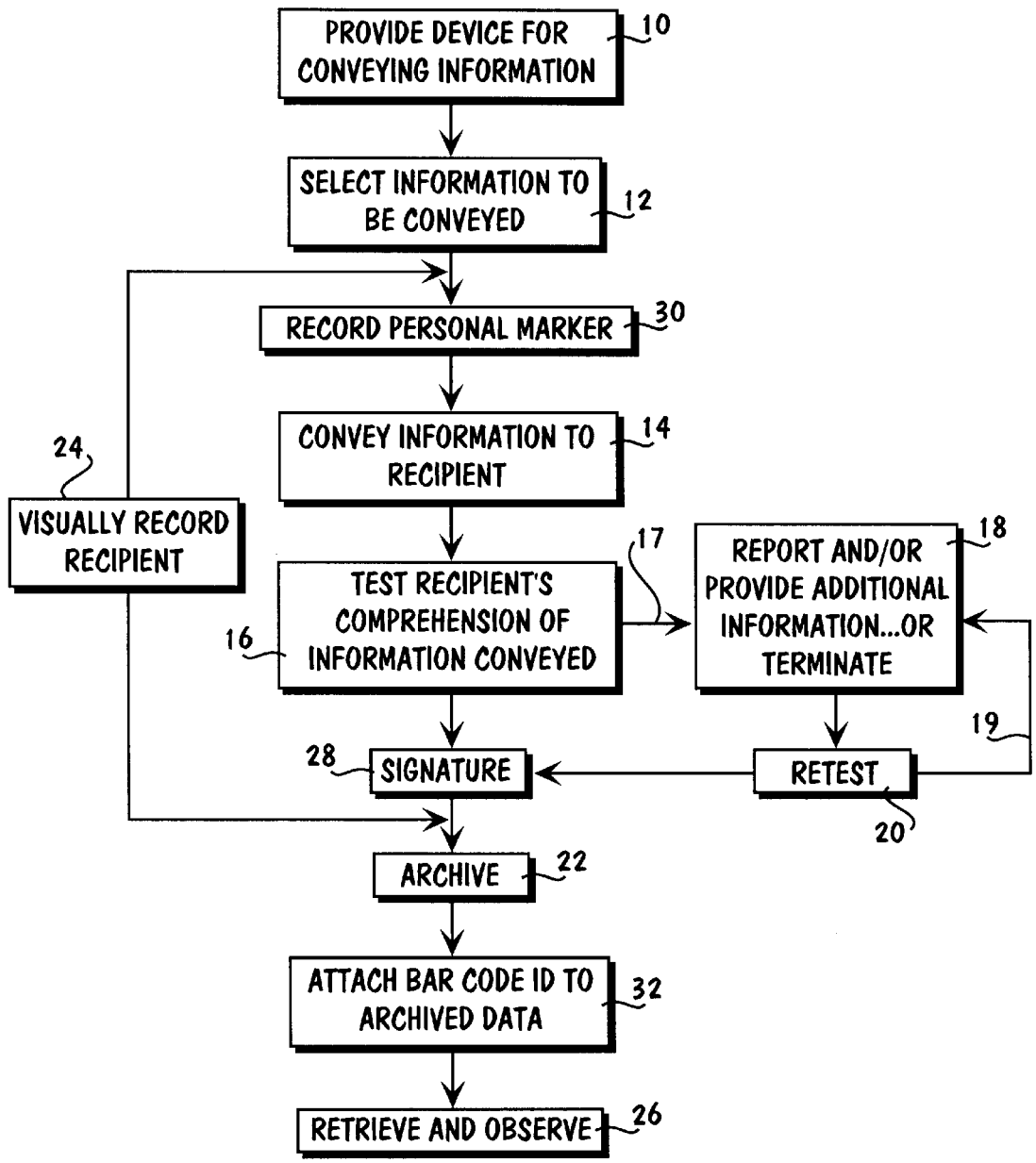
FIG. 1 is a flow diagram of the process of one embodiment of the present invention illustrating a method for authenticating a recipient's receipt and comprehension of information in accordance with the present invention.

Referring now to FIG. 1, there is shown a flow diagram of the process of one embodiment of the present invention illustrating a method for authenticating a recipient's receipt and comprehension of information in accordance with the present invention.

Referring now to block 10, a first step is to provide a device for conveying information to a recipient of such information. Such a device may include any means for providing information to a recipient, including but not limited to audio devices, visual devices, or preferably, audio-visual devices. Preferably such devices include a means for permitting the recipient to input information, such as responses to questions testing the recipient's knowledge of the information provided, as discussed in more detail below. Preferably, the device for conveying information is of the type which will limit the recipient's interaction with the process of the present invention to providing only permitted responses to specific questions so as to prevent the recipient from intentionally or inadvertently corrupting the integrity of the process of the present invention. A particularly preferred device is a touch screen associated with a computer-based system, which will enable the recipient to view the information provided and touch the screen to provide input, when input is sought by the process from the recipient.

Referring now to block 12, a second step in the process of the present invention is to select the information which is to be conveyed to the recipient. The information is typically selected by the entity seeking authentication of the recipient's receipt and comprehension of the information provided, and is selected, at least in part, based upon the activity in which the recipient will be engaged. For example, where the device for conveying the information is computer-based, it may contain information regarding several activities (e.g., several surgical operations and/or medications for medically based systems, although the present invention is in no way limited to the medical arts) whereupon the entity seeking authentication of the recipient's receipt and comprehension of the information provided (e.g., the physician or hospital or their agent) will select the appropriate information (e.g., surgical operation) relevant to the activity in which the recipient will be engaged which requires authentication of the recipient's informed consent.

The information is conveyed to the recipient as set forth in block 14. The information provided may be in simple narrative format requiring no input from the recipient, however an interactive system is preferred. As used herein, the term "interactive presentation system" refers to a system designed to present information to the participant as illustrated by block 14 and then prompt the participant with test questions regarding the information presented as illustrated by block 16. The participant views and listens to the presented information through a display means, preferably an audio-video monitor. As noted above, because the participant's interaction with the system should be limited due to security and data integrity concerns, the participant should indicate responses by touching a pressure or heat activated screen, (e.g., a touch screen). However, in instances where a touch screen is impractical or impossible to use, responses may be indicated by means of a computerized mouse, pressing built-in display buttons, or other conventional limited interactive means.

If the participant's responses indicate that the participant has insufficient comprehension of the information provided, the interactive presentation system may repeat all or selected portions of the information previously presented, present new information, terminate the learning session, or any combination thereof as illustrated by arrow 17 and block 18. For example, if the participant fails to obtain a predetermined score on a particular aspect of the presentation, a more detailed presentation of this aspect may be provided and the participant may then be re-tested as illustrated by block 20. If the retest again indicates that participant has obtained insufficient comprehension, the participant may be returned to block 18 as indicated by arrow 19 for one of the dispositions described above in connection with block 18. If the initial testing of block 16 or retesting of block 20 indicates the participant has obtained a required or desired level of comprehension or is unable to do so, the participant may be provided with additional information regarding the same or different subject matter (not illustrated in FIG. 1) or the process may be moved to the optional signature step illustrated in block 28 and described in more detail below or may be moved directly to the archiving step of block 22, also described in more detail below.

Where the information is presented in text form, the text may be written on an elementary school, for example, fifth grade, reading level to ensure comprehension across a broad section of the general population. Moreover, an option may be included to allow the participant to select interactive presentation text in a language the participant comprehends or, alternatively, which is subtitled and/or voice-over subtitled in a language the participant comprehends. The information presented may be uniquely created for each individual participant by the entity seeking the participant's informed consent, and may even include, where it is audio-visual in nature, presentations given by the entity, or its agents, seeking the authentication of informed consent. In the alternative, where standardization of the information provided is important, the provided information may include only standardized information which is provided with little or no modification to participants. In yet another embodiment of the present invention, the information provided may include both standardized information and information uniquely tailored to an individual participant.

The interactive presentation system may be audio, visual, or an audio-visual combination, preferably generated by means of a computer, but other methods of conveying information, such as real-time closed circuit or pre-recorded digital imaging may be used. Moreover, hand-held or portable devices are also envisioned, with or without the accompanying video.

As illustrated by block 24, the participant's interactions with the information provided, in particular where the information is provided via an interactive presentation, are preferably simultaneously recorded in real time via a visual recording means. The visual recording means is not limiting to the present invention, provided its output may be archived in the correlated fashion described below. Suitable camera's include video or still cameras. The camera may operate with traditional forms of developed film or it may be a digital camera, and may or may not simultaneously audibly record the participant. The visual recording equipment should contain tamper-resistant features, as, for example, complete enclosure in a protected structure. Preferably the visual recording equipment is also provided with a real-time clock and/or day/date function to record the date and/or time of the participant's interaction with the interactive presentation system. As may be appreciated, the visual recording equipment may be fitted with standard safety measures known in the art, including but not limited to low-light warning indicators, power failure warning indicators and other similar provisions. Moreover, in cases where a mobile interactive presentation-generating device is contemplated, fixed visual cameras can be replaced with mobile cameras. It is essential only that the visual recording equipment provide a visual record of the participant's interaction with the interactive presentation system which visual record can be archived on a storage medium in a correlated fashion along with the information provided and participant's responses to the testing conducted by the interactive presentation system. Moreover, in addition to, or in lieu of the visual record, a record may be made of other measurable biological functions or parameters of the participant, including but not limited to recordation of pulse rates, breath rates, blood pressure, nervous impulses/signals and the like which may likewise be archived on the storage media as discussed in connection with block 22 below. Such other biological functions or parameters may be measured in order to provide confirmation of the participants physical state during the participant's interaction with the interactive presentation system or to provide irrefutable proof the participant's participation with the interactive presentation where the biological function or parameter is unique to the participant (e.g., fingerprints, returned scans etc.). Alternatively, such biological functions may be measured for both purposes.

Figure 4:
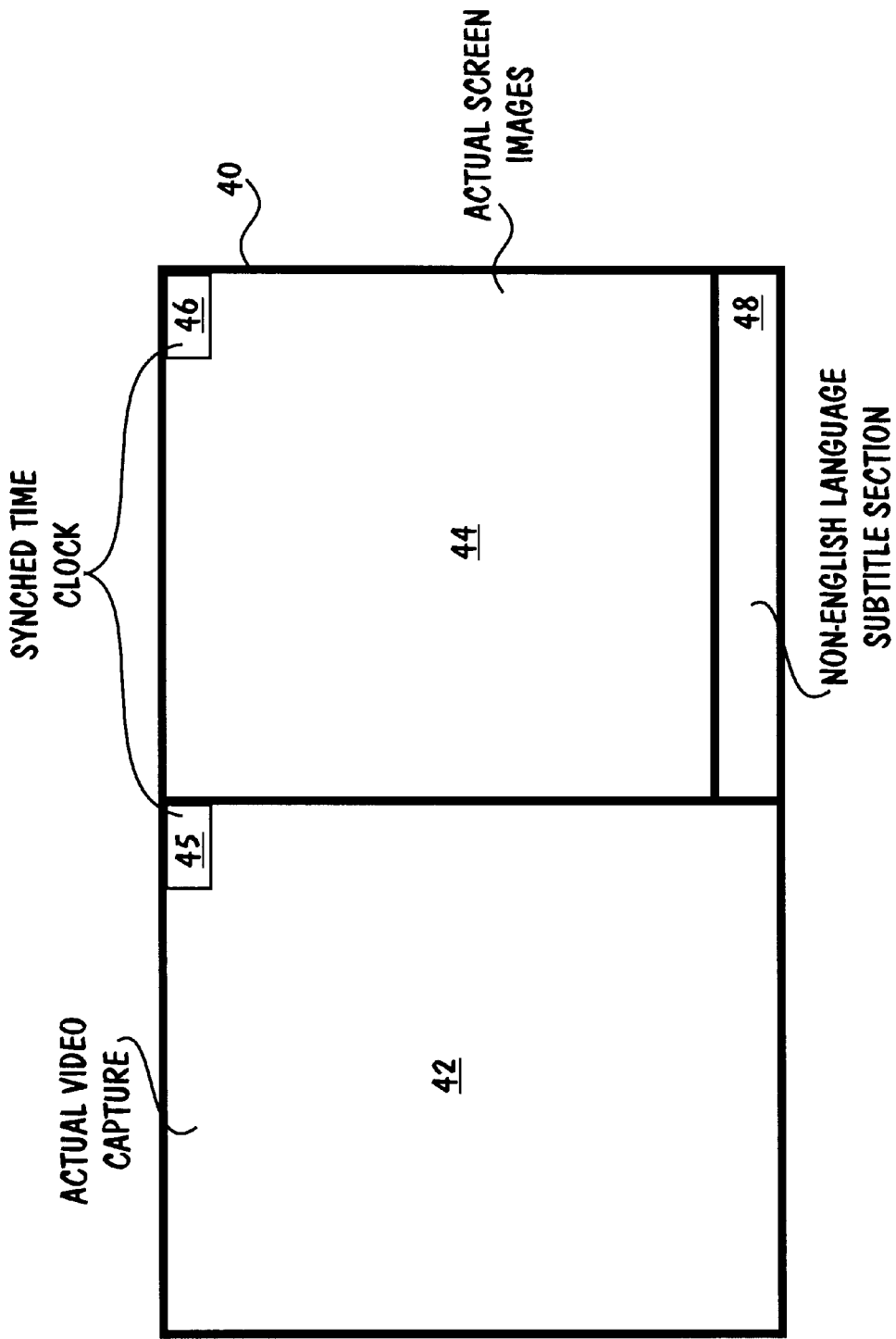
FIG. 4 is a diagram of a split-screen display device.

As illustrated by block 22, at the conclusion of the participant's interaction with the interactive presentation system, either by way of participant successfully demonstrating sufficient comprehension of the information provided or insufficient comprehension after repeated testing/ retesting cycles, both applicant's interaction with the interactive presentation system and the visual record are archived on a storage medium. (The optional signature step of block 28 is discussed below). In a preferred embodiment of the present invention, applicant's interaction with the interactive presentation system (e.g., the information provided, test questions provided and applicant's responses thereto) and the visual (and optionally audio-visual) record of the participant are archived on the storage medium in a correlated fashion. By correlated fashion it is meant that upon retrieval and observation, as illustrated by block 26, an observer is able to observe the information provided, test question provided and/or participant's response to the test question while simultaneously observing the visual record of participant's interaction with the information provided, test question provided or participants response thereto. In a particularly preferred embodiment of the present invention, as illustrated in FIG. 4, the record of participant's session may be displayed on an output screen in a split-screen format 40. Such a screen is split into two or more segments 42 and 44 preferably in such a way as to simultaneously view a real time video of the participant on one segment of the screen 42 while viewing the information conveyed, questions provided and the participants answers thereto on the other segment of the screen 44. A superimposed date-time clock 46 may be provided on either or both of the screen segments 42 and 44 to ensure the segments 42 and 44 are temporally simultaneous. Thus, one side of the output screen will display the images captured by the visual camera, in addition to the image of then recorded date-time clock. The other side of the output screen contains the entire interactive presentation as it occurred, including the participant's responses, as well as an image of the then recorded date-time clock. Additional information, including but not limited to information such as a text translation, the results of any system self tests, or subtitles may also be incorporated and displayed as for example, in one or more segments 48 illustrated in FIG. 4. It is to be understood that the manner of division of the screen is not limiting to the present invention, and the two segments may be provided in a side-by-side format, a top half-bottom half format, a picture-within-a-picture format or any other format known or later developed that permits simultaneous observation of the visual participation of the participant along with the information conveyed, questions provided and participants responses thereto. Also, as may be appreciated, such simultaneous observation is not limited to the visual record of the participant with the participants interaction with the interactive presentation, but may simultaneous visual observation along with measurable outputs of all of the participant's interactions with the various components of the present invention during the learning session, including but not limited to the participant providing the below described biological markers, signatures (written or electronic), inputting of personal data (e.g., name, address etc.,) as desired or required by the particular embodiment of the present invention.

The storage medium selected for the archiving process is not limiting to the present invention, and may include any known or hereafter developed storage media that are capable of recording the above described correlated record. Preferably, the storage media is durable, non-erasable and tamper-resistant or tamper proof. Suitable storage media include, but are not limited to, under presently available technology WORM (Write Once/Read Many) optical disk storage medium, CD-Rom disks, digital video disks, other laser video capture media, and tape back-up media including, but not limited to Zipp disks, Jazz disks, Syquest disks or others. Under presently available technology, read/write compact or optical disc provides a preferred storage media due to the large size of information that can be stored on a single disk and because of the durability of such disks over time. In one embodiment of the present invention, each participant's correlated record may be stored on a unique disk, or, in the alternative, provided sufficient steps are taken to protect the participant's confidentiality, particularly in applications of the present invention associated with the medical arts, more than one participant's record may be stored on a single disk.

In a preferred embodiment of the present invention, as illustrated in block 28, at the end of the learning session, the participant is prompted to provide his or her signature which is then also archived on the storage media. While under presently available technology the participant's signature could be included on paper or other media and digitized for inclusion on the storage media, it is preferred to have the participant provide his or her signature via an electronic means, such as a light pen or pressure pad. Where the participant's interaction with the interactive presentation system indicates the participant gained a desired or required level of comprehension of the information presented, their signature may be taken as another indicia of the participant's understanding of the information provided and participant's willingness to assume such risks as were disclosed by the information provided. Where the participant's interaction with the interactive presentation system indicates the participant did not gain a desired or required level of comprehension of the information presented, their signature may at least be taken as evidence that the participant engaged in the learning session.

As illustrated by block 30, if uncontrovertible proof is required or desired that participant did engage in the learning session, participant may be requested or required to provide in lieu of or in addition to the above described signature, a uniquely personal marker which is recorded and archived as described in connection with block 22. Such uniquely personal markers include, but are not limited to biological markers, which in turn include but are not limited to fingerprint(s), toe/foot print(s), corneal scans, retinal scans and the like. While block 30 has been shown in the flow diagram of FIG. 1 as occurring before the information is conveyed to the participant, as may be appreciated, it is not limited to that position in the flow chart but may occur and any stage before the archiving step of block 22.

Where the archived record of one or more participants is maintained on storage media that is comprised of a plurality of discrete units (e.g., optical or compact disks), it is preferable to label such discrete units for ease of filing and retrieval of the individual units. Such labels are not limited by the present invention except that they must be compatible with the selected storage media so as not to interfere with the retrieval of the information on the storage media. Further, it is preferred that such labels are durable and permanently affixed or otherwise associated with the storage media. For example, where the storage media is comprised of optical or compact disks, the label may take the form of a hand written, typed or computer-generated gummed label affixed to the optical or compact disk or to a storage case for such a disk.

Such labeling should include sufficient identifying material for filing and retrieval of a particular unit. While the label could simply include information about the participant, i.e. name, address etc., in text or written form, it is preferred to provide a labeling system which protects the confidentiality of the participant's record. For example, where the label includes information, such as the name, address etc. of the participant in visually observable texture or written form, at least those individuals involved in the filing and retrieval of the storage media will be able to read the label and associate an individual participant with his or her record. In order to prevent this and to protect the confidentiality of the participant, the identifying material on the label may take the form of an alpha, numeric, alpha-numeric system or other system which identifies the individual participant and provides the desired information on the label in such a way as not to be readable or comprehendible by individuals observing the label. With such a system, the participant is then only identified by comparing the identifying material on the unit with a table or other data collating system which correlates the identifying material with an individual participant, and access to such a table may be restricted to protect the participant's confidentiality.

In an alternative embodiment of the present invention, the units of the storage media may be provided with bar-coded identification tags as illustrated by block 32 in FIG. 1. Bar-coded identification tags are preferred because they protect the participant's confidentiality and further are compatible with many automated storage and retrieval devices which automatically store and retrieve by reading such bar-coded information. However, as may be appreciated the present invention is not limited to the above described gummed labels or bar-code tags, but includes any identification means which does not interfere with the storage media's ability to store and retrieve data and which can be caused to provide the required or desired identifying material.

Protecting participant's confidentiality according to the present invention is not limited to the labeling/bar-code discussion above, but includes any confidential record management system, apparatus or processes for providing secure, confidential management of the participant's record.

It is within the scope of the present invention to provide a permanent archiving apparatus at the same physical location or site as the information conveying device and visual and interactive presentation recording devices. For purposes of the following discussion, unless otherwise clear from the context, the information conveying device, visual recording and interactive recording devices are hereinafter collectively referred to as the "information conveying/recording operation", which term excludes the archiving operation.

As may be appreciated, with presently available technology, archiving such information as described above, particularly where such information includes digitized video information, can be memory intensive, using the term "memory" as is conventionally used to refer to computer-based memory including random-access memory, read only memory and the memory associated with storage devices such as hard disks, floppy disks, Zipp disks and the like. Further, it may be more efficient and economical in certain instances to provide a central location for receiving such digitized records and down-loading the records to the selected storage media. Certainly this results in requiring fewer archiving devices where the information is provided to participants at different sites, such as for example, in the various departments of a hospital or at different hospitals within a given hospital system. Further, where participant confidentiality is a concern, it is preferable to provide a central location for receiving such records, particularly where the storage media units are provided with identifying material which does not specifically identify an individual participant by name or address. With such a centralized system, personnel involved in archiving the data are substantially removed from the participant ensuring an additional layer of confidentiality for the participant.

However, where the information conveying/recording operation and the archiving operation are conducted at different sites, the transmission of the record of the learning session from one site to the other raises certain concerns. Among those concerns is that the transmitted data must be transmitted rapidly, inexpensively, free of errors, and, where confidentiality is a concern, with sufficient security. In addition, it is preferred that at least temporary archiving be conducted at the site of the information conveying/recording operation until confirmation is received of the receipt and error-free archiving of the record at the site of the permanent archiving operation. In a preferred embodiment of the present invention, the session records, whether or not temporarily archived, are downloaded through electronic means, as for example, through the Internet, a dedicated local area network, leased private or semi-private data transmission lines or the like and/or combinations thereof, using encryption or other secure means, to the site of the permanent archiving operation, hereinafter, "the record repository". It is preferred that the record repository also have security procedures in place to safeguard and limit access to the records stored therein.

Figure 2:
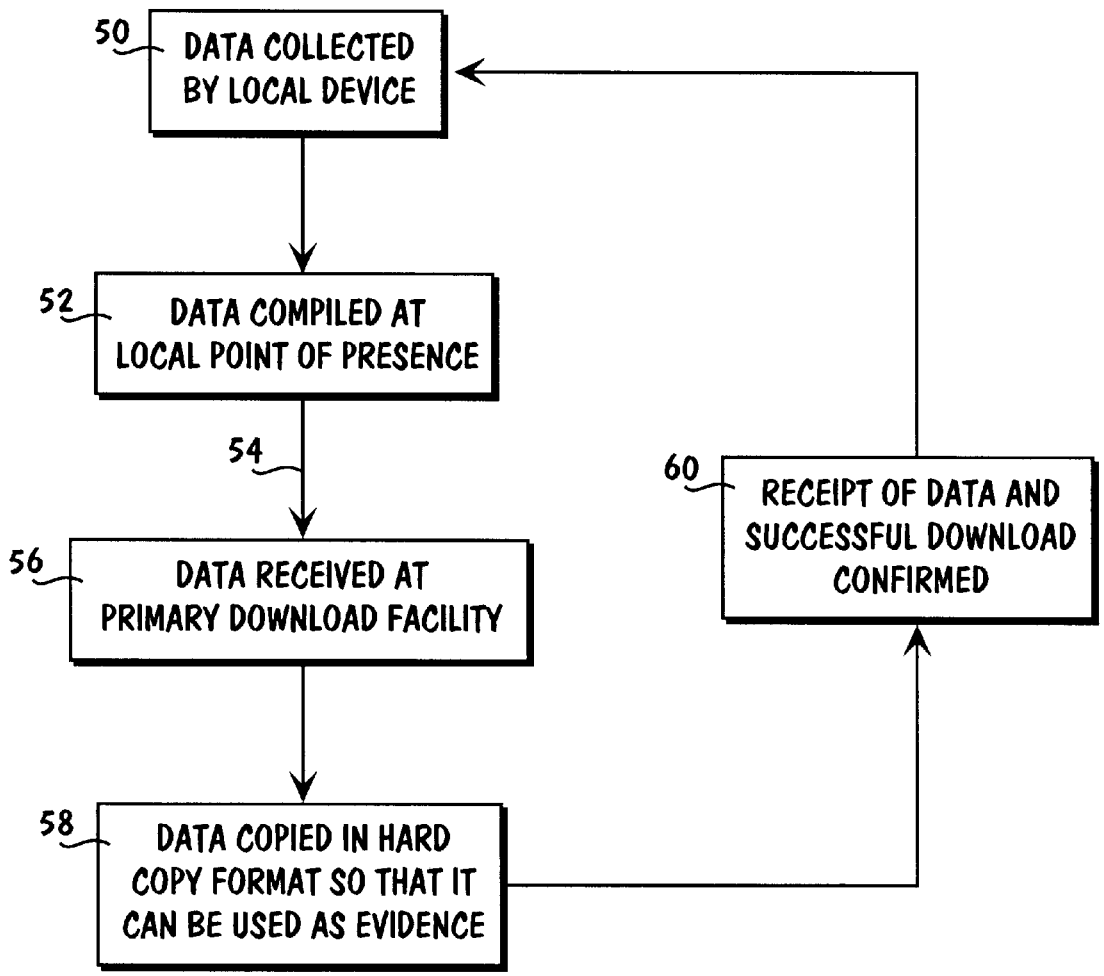
FIG. 2 is a flow diagram of the operation of an embodiment of the present invention where the collected data is relayed to a remote storage facility.

Illustrated in FIG. 2 is a flow diagram of one embodiment of the present invention illustrating downloading of the session record to a record repository. In this embodiment, session data is collected by the information conveying/recording device as illustrated by block 50 which data may be compiled at the same site as illustrated by block 52. The data is then conveyed electronically in the manner described above, preferably with security (e.g., encryption and the like) as illustrated by the arrow 54 to a second site which is the record repository. The encrypted data is received at the record repository as illustrated by block 56, whereupon it is archived on the storage media as illustrated by block 58. In a preferred embodiment of the present invention, not illustrated in FIG. 2, the data is at least temporarily archived at the first site until receipt and confirmation of a successful downloading at the record repository is transmitted to the first site, as illustrated by block 60. Upon receipt of the above described confirmation, the temporarily archived data at the first site may be optionally erased or otherwise destroyed. In the alternative, the data may be permanently archived at both the first and second site to provide a redundant system. However, where confidentiality of the record is a concern, steps similar to those outlined above with regard to protecting the participant's confidentiality should be maintained at both the first and second sites.

Figure 3:
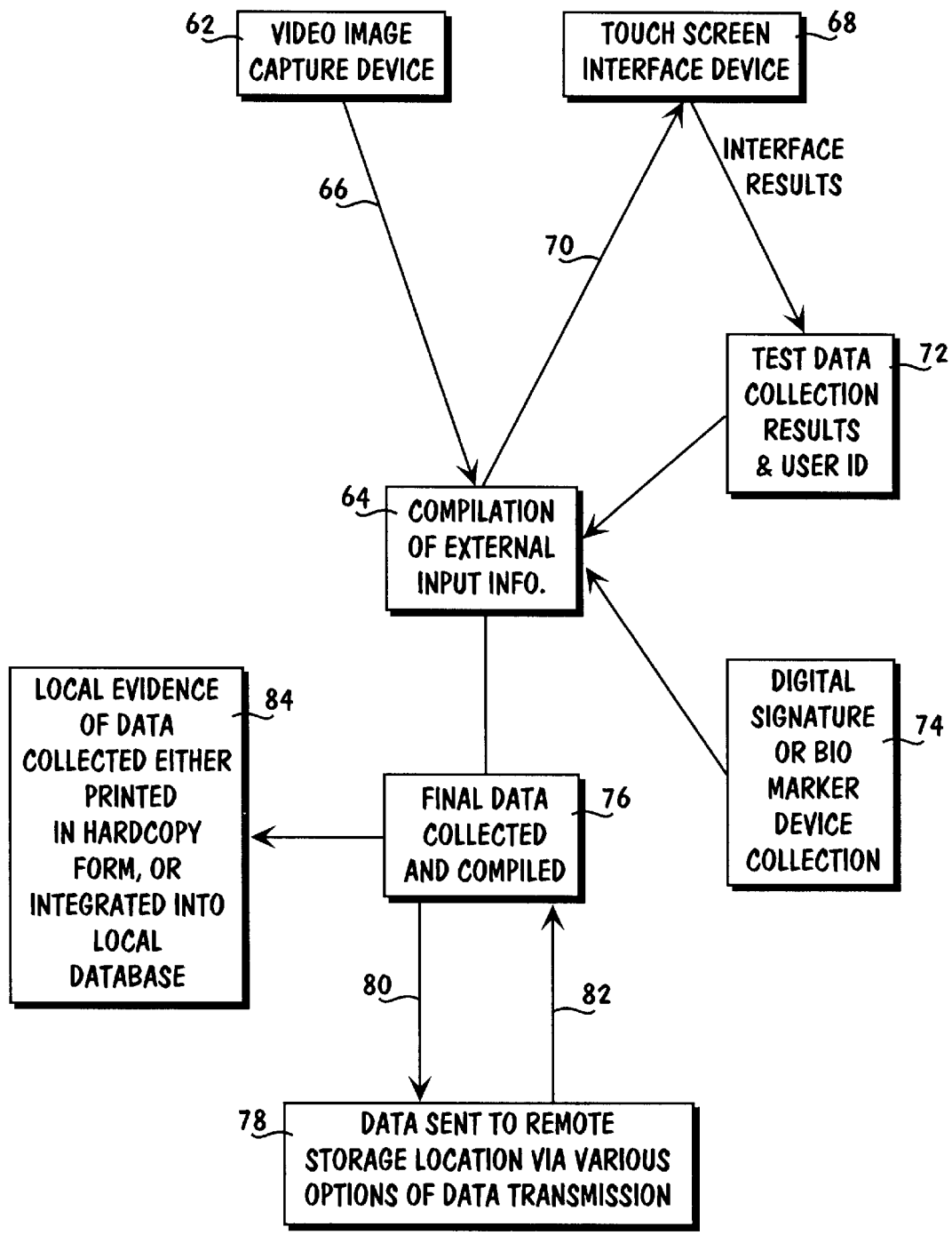
FIG. 3 is a schematic diagram of one embodiment of the apparatus for obtaining informed consent of the present invention.

Referring now to FIG. 3 there is shown a general schematic diagram of the apparatus that may be used in one embodiment of the present invention. A visual image capture device (e.g., a digital video camera) 62 is connected to an information conveying/recording device 64 (e.g., a computer) in such a manner as to enable the visual image capture device to download its visual record as illustrated by arrow 66 to the information conveying/recording device 64. The information conveying/recording device 64 provides selected information to an output device 68 (e.g., an audio/visual monitor) as illustrated by arrow 70. Such information may be in a narrative form or in the form of an interactive presentation as described above. Where the information is of the interactive presentation form, the output device 68 is preferably fitted with an input mechanism to receive input from a participant as appropriate during the interactive presentation. An example of a suitable input device is the touch screen described above. The information conveying/ recording device 64 provides, in the interactive presentation form, among other things, testing inquiries which require a response by a participant. The test data may then be returned to the information conveying/recording device 64 directly (not shown) or such test data may be conveyed to a data collection device 72 (e.g., a computer or other high speed access digital media storage device) which in turn relays the test data to the information conveying/recording device 64. The information conveying/recording device 64 may, optionally, be in communication with a marker device 74 (e.g., a digital signature device or biological marker device) to input such authenticating information from the marker device 74 into the information conveying/recording device 64. The recorded visual information and test data may be compiled in a correlated fashion on an onsite archiving device 76. Preferably the information conveying/recording device 64 is provided with a real-time clock and a day/date indicator which records the date and time of the recording of both the visual record and the participant's interaction with the interactive presentation system for subsequent display as described above in the discussion directed to FIG. 4. The archiving device 76 may provide temporary or permanent archiving. In a preferred embodiment, the correlated record is sent to the record repository 78 at a second site via the data transmission devices described above as illustrated by the arrow 80, which in turn provides confirmation of an error-free receipt back to the archiving device 76 as illustrated by the arrow 82. In yet a still more preferred embodiment of the present invention, a device 84 for evidencing collection of the visual and interactive presentation data at the first site may be in communication with the archiving device 76 to provide confirmation of the record collection at the first site. Such evidence may be in the form of a printed hardcopy notice or by updating a database associated with the device 84. Not shown in FIG. 3 is an encryption device which may be a separate unit from any of the units described above or which may simply be incorporated into one of the above described devices, as for example the archiving device 76 or the information conveying/recording device 64.

Figure 5:
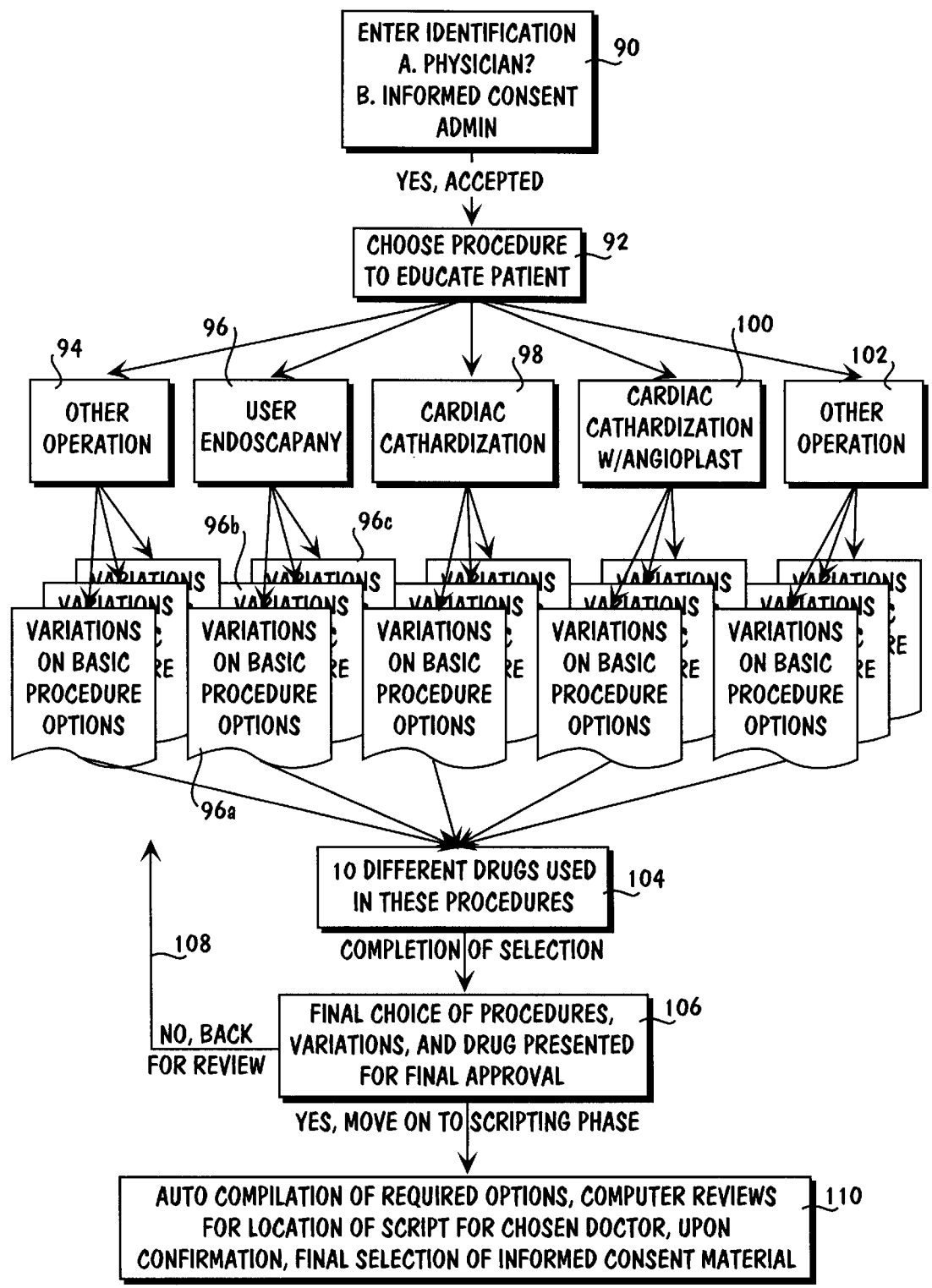
FIGS. 5 and 5A are flow diagrams of the operation of an embodiment of the present invention related specifically to providing information of a medical nature and obtaining authenticated informed consent in a medical context.
Figure 5A:
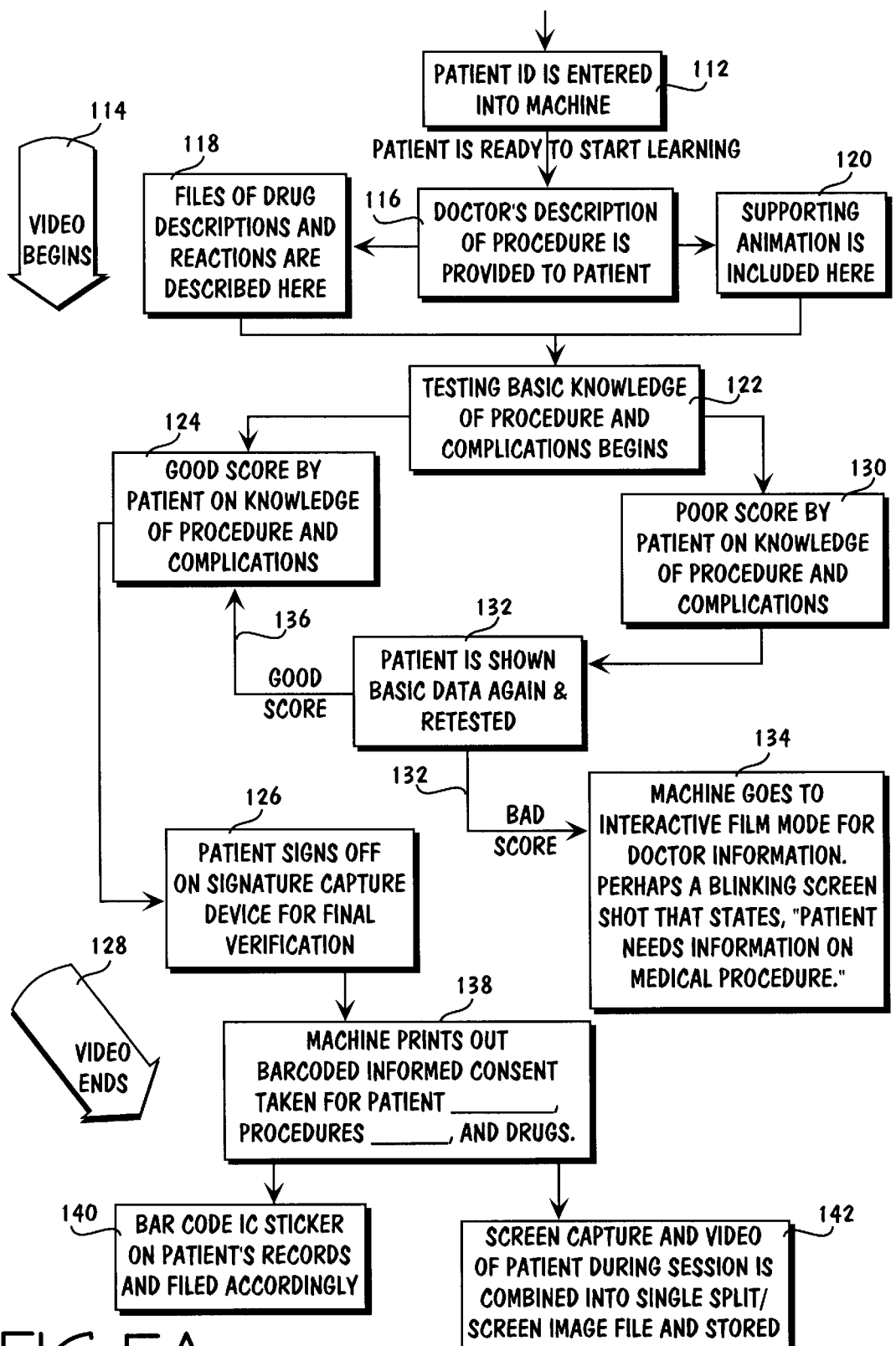

FIGS. 5 and 5A are general flow diagrams of the operation of the present invention in a medical application, more particularly in an application where a physician seeks to obtain the informed consent of a patient to perform a surgical operation on the patient.

In a preferred first step illustrated by block 90, either the physician or administrator in charge of the learning session must enter identifying information before the system of the present invention may be activated. In the following discussion the term physician will be used for the sake of brevity, but it is to be understood that administrators or other individuals qualified and authorized to administer the system are to be included within that term. By requiring the inputting of identifying material in order to activate the system the integrity of the system and protection from intentional or inadvertent corruption is minimized. If the identifying information for the physician is accepted, the physician is then prompted or permitted to select the information desired to be conveyed to the patient, as illustrated by block 92. Illustrated in FIG. 5 are but a few of the possible surgical procedures about which information may be conveyed to a patient as illustrated by blocks 94, 96, 98, 100 and 102. As illustrated by blocks 96a, 96b and 96c, information regarding common variations on the basic surgical procedure may also be included in the system of the present invention. As noted above, such information regarding the surgical procedure may be previously inputted by the individual physician, as by way, for example, of textual material, visual material or audio-visual material which may or may not be tailored for an individual patient. Alternatively, in lieu of or in addition to, information regarding the surgical procedure and its variations may be those which are standardized to ensure that each patient received the same information where standardization is desired or required. Where standardized information is selected, one important advantage of the present invention is that the results of the testing of several patient's understanding of such information can be examined by the testing described below, to identify which standardized presentations are being readily understood by the majority of patients and, conversely, identifying those which are not. The information may be narrative, or preferably is provided as an interactive presentation maintained on a device suitable for the storage and presentation of such information, such as a computer and/or computer database. When the subject matter has been selected for the patient by the physician, additional information, as for example, information regarding the drugs to be used in the selected surgical procedure may also be provided as part of the interactive presentation as illustrated by block 104. A final overview of the procedure, any variations, and the drugs involved are then presented for final inspection to the physician as illustrated by block 106. If the information in the final overview is defective, the process can be returned to the selection of subjects and the above described process repeated as illustrated by the arrow 108. If the final overview contains the correct information, the physician approves the selection and the appropriate information is prepared for presentation to the patient. More particularly, a scripting phase 110 is initiated, comprising an auto-compilation of the options specified above in terms of the information the physician has selected for presentation to the patient.

After the information has been compiled by the information conveying device, or while the device is compiling the relevant information during the scripting operation, either the patient or the physician may enter information identifying the patient, such as the patient's name, address, phone number, social security number and the like, or the physician or patient may enter a patient identification number in addition to or in lieu thereof for confidentiality purposes, as illustrated by block 112. Optionally, the patient may be asked to confirm the accuracy of the personal information, whereupon an affirmative response may be utilized to activate other features of the invention, including but not limited to the activation of a system self-diagnostic test of the critical system components. Other features, such as a tamper indicating encryption stamp, or other method to identify intentional or unintentional corruption of the data selected to be presented to the patient or the patient's responses thereto can also be added/activated. The patient's responses to these and subsequent questions described below, like the presentation itself, may be recorded simultaneously with a visual record of the patient's interaction with the questions, in real time, along with a running date-time clock to authenticate the presentation to the patient and the patient's response thereto.

At this point, the patient is prepared to start learning and the information is conveyed to the patient. Where the information being provided includes visual, including but not limited to video information, the visual information would start to be provided to the patient as indicated by the arrow 114.

The interactive presentation presents the pre-selected subject chosen in the previous steps. An introduction by the physician overseeing or performing the procedure may be presented along with a description of the procedure as illustrated by block 116. Where drugs are to be administered, drug descriptions may be provided as illustrated by block 118 may be provided. Similarly, where supporting audio, graphics, animation or the like is to be provided, such information may also be conveyed to the patient at this point, as illustrated by block 120.

Either before (as an assessment of the patients preliminary level of understanding) during or after or combinations thereof, of the course of the interactive presentation, the participant may be asked questions by the interactive presentation regarding the subject presented as illustrated by block 122. If the patient through the test scores i.e. answers a selected number of the questions correctly, indicates a desired or required level of comprehension of the material presented, as illustrated by block 124 the patient is directed at the end of such presentation to provide his or her signature, preferably electronically by way of a digital signature device 126 and the presentation of information, including video information ends as illustrated by arrow 128.

However, if the patient's test score is not satisfactory as illustrated by block 130, either repeated or new information regarding the relevant subject matter is provided as illustrated and the patient is retested as illustrated by block 132. While not shown in FIG. 5A, as may be appreciated, utilizing a series of questions during the presentation of the information can help to identify with particularity where the patient is not comprehending the information provided and to confirm those areas where comprehension is satisfactory, which in turn permits presentation of additional reinforcing information in block 132 of a very focused nature directed to the patient's specific areas of unsatisfactory comprehension. If the participant's retesting score is again unsatisfactory after a pre-programmed number of re-education attempts, the interactive presentation session is terminated. Preferably at this point, a medical professional is summoned or otherwise consulted, and individual counseling may be provided to the patient, preferably while the visual or audio/visual recording continues as illustrated in block 134. The patient may be returned to the interactive system if warranted in the opinion of the physician, or such individual counseling may take the place of any further patient interaction with the interactive presentation. In the alternative, with a satisfactory retesting score the patient is moved to block 124 as illustrated by arrow 136, whereupon the patient provides his or her signature in the manner described above in connection with block 126.

After the participant has signed his or her name, the interactive presentation ends. In a preferred embodiment of the present invention, the session data, including the interactive presentation provided to the patient and the visual record of the patient's interaction with that interactive presentation is archived in the correlated fashion described above, preferably including a real-time clock and day/date indicia for each to ensure synchronized playback as described above, and the storage media on which the record is archived is provided with identifying information, preferably in the form of a bar-code tag affixed to the storage media as illustrated by block 138. The identifying material may include information summarizing the patient's identifying information or number, the surgical procedure presented and/or the drugs described either by way of textual material or by way of the appropriate codes embedded in the bar-code tag. Other pertinent information may be included as well, including but not limited to the date and time the information was presented, which physician presented the information and the like.

In a preferred embodiment of the present invention, two bar-code tags, preferably identical tags, are provided as illustrated in block 140. The first bar-code tag attached to the storage media, e.g., a non-erasable video or digital record of the learning session. The second bar-code tag is affixed in the patient's written and/or electronic medical records to provide confirmation in the patient's record that the patient was provided with the information for which the physician sought the patient's informed consent. The record of the session may be archived at the site of information conveyance or may be transmitted to an off-site record repository as described above. Where the session record is transmitted off-site, the bar-code tag (or other labeling system) may include information confirming that the patient's session was encrypted before transmission. In yet another embodiment of the present invention, where the record is not transmitted but is permanently archived at the site of information conveyance, the record may be encrypted to increase patient confidentiality. Further, where the off-site record repository is designed to provide confirmation of successful receipt and downloading back to the original site of information conveyance, such confirmation may be provided in several forms, including a written form, which is also placed in the patient's written medical file.

Subsequently, when observation of the record is required or desired, the information may be retrieved and displayed in the split-screen format described above and as illustrated in block 142.

In sum, the process shown in FIGS. 5 and 5A generally comprises the steps of: (1) energizing an interactive presentation; (2) entering administrative information into the interactive presentation permitting the physician to interface with the system; (3) re-entering administrative information if required; (4) choosing a desired subject matter for presentation; (5) explaining collateral subject matter related to the subject matter selected; (6) presenting a final overview of the desired subject and any collateral subject matter for acceptance by the physician; (7) entering a scripting phase to collate the information selected by the physical for presentation to the patient as an interactive presentation; (8) compiling any required options into the presentation; (9) completing the scripting phase; (10) entering a patient's identification data into the interactive presentation; (11) positioning a patent before the interactive presentation to prepare the patent to interact with the interactive presentation; (12) conveying the scripted information to the patient, preferably from a video and data recording means while simultaneously visually or otherwise recording the patient and recording the information presented during the interactive presentation and recording the patients inputted responses to questions regarding the information presented as described below; (13) providing a means for the patient to input data in the form of answers to questions regarding the information presented to test the patient's comprehension of the information presented; (14) prompting the participant to answer a series of pre-formatted questions; (15) repeating portions of the interactive presentation with the same information, new information or combinations thereof if the patient's number of correct answers is below a predetermined threshold; (16) terminating the interactive presentation if the patient continues to perform below the predetermined threshold or if the patient's number of correct answers is above a predetermined threshold; (17) prompting the patient for an electronic signature; (18) stopping the data and video recording means; (19) printing identifying, preferably bar coded labels; (20) positioning a bar coded label on the participant's medical records; (21) making a consolidated, correlated non-erasable, tamper-resistant record of the video, the interactive presentation transactions, and authenticating information; (22) optionally making a backup copy of the consolidated, correlated non-erasable, tamper-resistant record; (23) encrypting the non-erasable, tamper-resistant record; (24) downloading the consolidated non-erasable, tamper-resistant record; and (25) positioning a bar coded label on the consolidated non-erasable, tamper-resistant record.

As noted above, while the above-described description of the invention was directed specifically to a medical application for purposes of illustration, the invention is by no means limited to medical applications. The method and apparatus of the present invention can also be used in conjunction with many other completely unrelated activities wherever authentication of the conveyance and understanding of information from one party to another is required or desired. Non-limiting examples including requiring informed or knowing consent or waiver of the assumption of risks associated with activities such as renting jet skis or other watercraft, driving or renting sports cars, skydiving, horseback riding, the effects of receiving Miranda warnings, the effects of submitting to breathalyser examinations, to name but a few examples. Therefore, the particular embodiment of the invention described above should not be considered as limiting to the scope of the invention.

It can therefore be seen that the present invention provides an apparatus and a method of employing the apparatus to educate, confirm exposure to and comprehension of the educational material, to provide a permanent record of the same including the ability to authenticate the integrity of the record, add credibility to the process used to create and provide the record, and help ensure individual privacy rights. The apparatus uses an interactive presentation to facilitate a participant's comprehension while simultaneously creating a non-erasable, tamper-resistant record which can be stored separately or encrypted and sent to a remote location. The invention provides a process applicable to a broad range of activities and provides evidence and proof of understanding of the risks involved with such activities and a fully-documented, informed consent process which is customizable and individual in focus.

Although the invention has been described in terms of preferred embodiments, it will be understood that numerous variations and modifications may be made without departing from the spirit and scope of the present invention as described above and as set forth in the accompanying claims.

What is claimed is:

1. A method for authenticating a recipient's receipt and comprehension of information comprising the steps of:
   a) providing a device for conveying information to a recipient;
   b) selecting information to be provided to the recipient by the information conveying means;
   c) recording at least one uniquely personal marker of said recipient to establish recipient's exposure to said information;
   d) conveying said information to said recipient;
   e) providing said recipient with at least one inquiry selected to determine said recipient's comprehension of the information conveyed;
   f) directing said recipient to provide an answer to said inquiry;
   g) recording each of said information conveyed, said inquiry and said recipient's answer to said inquiry while simultaneously visually recording said recipient as said recipient reviews said conveyed information, said inquiry and provides said answer; and
   h) correlatedly archiving on a storage medium said conveyed information, said inquiry, said answer and said visual recording of said recipient such that said conveyed information, said inquiry, said answer and said visual recording of said recipient are retrievable to simultaneously observe at least one element selected from the group consisting of said conveyed information, said inquiry, said answer and the corresponding visual record of said recipient reviewing said conveyed information, said inquiry or providing said answer.

2. An apparatus for authenticating a recipient's receipt and comprehension of information comprising:
   a) a device for conveying information to a recipient;
   b) a means for selecting information to be provided to the recipient by the information conveying means;
   c) a means for recording at least one uniquely personal marker of said recipient to establish recipient's exposure to said information;
   d) a means for conveying said information to said recipient;
   e) a means for providing said recipient with at least one inquiry selected to determine said recipient's comprehension of the information conveyed;
   f) a means for directing said recipient to provide an answer to said inquiry;
   g) a means for recording each of said information conveyed, said inquiry and said recipient's answer to said inquiry;
   h) a means for simultaneously visually recording said recipient as said recipient reviews said conveyed information, said inquiry and provides said answer; and
   i) a means for correlatedly archiving on a storage medium said conveyed information, said inquiry, said answer and said visual recording of said recipient such that said conveyed information, said inquiry, said answer and said visual recording of said recipient are retrievable to simultaneously observe at least one element selected from the group consisting of said conveyed information, said inquiry, said answer and the corresponding visual record of said recipient reviewing said conveyed information, said inquiry or providing said answer.

3. A system for conveying information and providing confirmation of its receipt by at least one recipient comprising:
   an information relaying device for providing preselected information to the recipient; and
   an image retention system coupled to the information relaying device, wherein the image retention system contemporaneously records images of the recipient viewing the preselected information as the preselected information is displayed to the recipient.

4. The system as recited in claim 3, wherein the information relaying device includes audio and video display equipment.

5. The system as recited in claim 3, wherein information relaying device includes an interactive presentation system that provides the preselected information to the recipient and requests at least one response from the recipient for providing an indicator corresponding to a relative level of comprehension for the preselected information by the recipient.

6. The system as recited in claim 5, wherein the interactive presentation provides an educational information session for a medical procedure to obtain informed consent.

7. The system as recited in claim 5, wherein the interactive presentation system includes an input mechanism for receiving prompted input from the recipient during the course of displaying the preselected information.

8. The system as recited in claim 7, wherein the input mechanism is a touch screen monitor.

9. The system as recited in claim 3, wherein the information relaying device includes a narrative presentation.

10. The system as recited in claim 3, wherein the information relaying device includes a video and graphic presentation.

11. The system as recited in claim 3, wherein the image retention system includes a memory storage device for storing the information relayed to the recipient and the correlated images of the recipient observing the delivery of the relayed information.

12. The system as recited in claim 11, wherein the memory storage device is in communication with an optical disk storage medium.

13. The system as recited in claim 3, wherein the image retention system includes a video camera that synchronously records the images of the recipient during delivery of the relayed information to the recipient.

14. The system as recited in claim 13, wherein the images of the recipient and the display of the relayed information are time stamped.

15. The system as recited in claim 3, wherein the image retention system includes an input device for recording a personal marker unique to the recipient.

16. The system as recited in claim 3, wherein the input device is a signature capture device.

17. The system as recited in claim 3, wherein the image retention system includes measurement apparatus for detecting and contemporaneously recording selected parameters associated with the reactions of the recipient.

18. A system for retrieving archived information and displaying its receipt by at least one recipient comprising:
    an information storage device for storing an archival record that includes preselected information provided to the recipient and correlated images of the recipient viewing the preselected information as the preselected information is provided to the recipient; and
    a display monitor for simultaneously displaying the archival record of the preselected information and the correlated images of recipient receiving the preselected information.

19. The system as recited in claim 18, wherein information storage device further stores an interactive presentation record that includes the preselected information to the recipient and at least one response from the recipient that provides an indication as to the level of comprehension of the preselected information by the recipient.

20. The system as recited in claim 19, wherein the interactive presentation record is contemporaneously displayed on the display monitor with the archival record.

21. The system as recited in claim 18, wherein the information storage device is an archival repository.

22. The system as recited in claim 21, wherein a plurality of archival records are stored in the archival repository, and wherein an identifying label is provided for each archival record that uniquely corresponds to the record.

23. The system as recited in claim 18, wherein the record includes an audio and visual record of the preselected information and the correlated images of the recipient viewing the preselected information.

24. The system as recited in claim 23, wherein the audio and visual record is displayed in a split-screen format.

25. A computer-based information storage and retrieval system for providing confirmation of relayed information comprising:
    a computer having a processor and a memory storage device, wherein the memory includes a program for generating an interactive presentation that displays preselected information to the recipient, and wherein the computer is adapted to receive at least one prompted input response from the recipient to demonstrate a level of comprehension of the preselected information by the recipient;
    a visual recorder coupled to the computer, wherein the visual recorder contemporaneously records a visual record of the recipient observing the preselected information within the interactive presentation as the preselected information is provided to the recipient;
    a memory storage device in communication with the visual recorder for storing the visual record, wherein the visual record includes the preselected information within the interactive presentation provided to the recipient and correlated images of the recipient viewing the preselected information as the preselected information is provided to the recipient; and
    a display monitor for simultaneously displaying the visual record including the preselected information within the interactive presentation and the correlated images of recipient receiving the preselected information.

26. The computer-based information storage and retrieval system recited in claim 25, wherein the interactive presentation includes a graphical user interface that displays the preselected information.

27. The computer-based information storage and retrieval system recited in claim 26, wherein the graphical user interface includes prompts for receiving the prompted input response from the recipient while the preselected information is provided to the recipient.

28. The computer-based information storage and retrieval system recited in claim 26, wherein the display monitor is configured to simultaneously display the preselected information and the visual record of the recipient receiving the preselected information.

29. The computer-based information storage and retrieval system recited in claim 26, whrein the memory storage device is a hard-disk drive, and wherein the visual record is locally stored on the hard-disk drive.

30. The computer-based information storage and retrieval system recited in claim 26, further comprising a central record repository with optical disk drives in communication with the hard-disk drive for archived information storage.

31. The computer-based information storage and retrieval system recited in claim 25, further comprising a real-time monitor of the visual record and the interactive presentation as it is presented to the recipient.

* * * * *